(12) United States Patent
Wyatt et al.

(10) Patent No.: US 7,629,165 B2
(45) Date of Patent: *Dec. 8, 2009

(54) DIAGNOSTIC DEVICE AND METHOD

(75) Inventors: James Wyatt, San Diego, CA (US);
Matthew Scott, Oceanside, CA (US);
Vijay Mahant, Murrieta, CA (US)

(73) Assignee: Qualigen, Inc, Carlsbad, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 10/544,738

(22) PCT Filed: Jan. 22, 2004

(86) PCT No.: PCT/US2004/001982

§ 371 (c)(1),
(2), (4) Date: May 24, 2006

(87) PCT Pub. No.: WO2004/073486

PCT Pub. Date: Sep. 2, 2004

(65) Prior Publication Data

US 2007/0077604 A1   Apr. 5, 2007

(51) Int. Cl.
*C12M 1/34* (2006.01)
(52) U.S. Cl. ............... 435/287.3; 435/7.1; 435/7.25; 435/287.2; 435/288.2; 435/288.5; 435/288.7; 436/47; 436/164; 436/165; 436/172; 422/63; 422/68.1; 422/82.05; 422/82.09

(58) Field of Classification Search ............... 435/4, 435/7.2, 7.25, 287.2, 288.2, 288.5, 288.7, 435/7.1, 287.3; 436/47, 63, 164, 165, 166, 436/172, 177, 179, 501, 807; 422/55, 58, 422/63, 68.1, 82.05, 102, 103, 82.09
See application file for complete search history.

(56) References Cited

U.S. PATENT DOCUMENTS 6,084,660 A * 7/2000 Shartle ............... 356/39
6,300,138 B1 * 10/2001 Gleason et al. ......... 436/165
6,818,180 B2 * 11/2004 Douglas et al. .......... 422/58

* cited by examiner

*Primary Examiner*—Gailene R Gabel
(74) *Attorney, Agent, or Firm*—Fish & Associates, PC

(57) ABSTRACT

A method of separating a cell-containing sample into a substantially cell-depleted portion, and a cell-containing portion comprising at least one of a stem cell, a lymphocyte, and a leukocyte comprises a step in which the sample is received in a vessel with at least one flexible wall. In another step, an additive and particles are added to the sample, wherein the additive substantially binds to the at least one of the stem cell, lymphocyte, and leukocyte, and the particles and wherein the particles substantially bind to the at least one of the stem cell, lymphocyte, and leukocyte, and the additive, thereby producing a cell-containing network. In a further step, the network is separated from the substantially cell-depleted portion by applying a magnetic force.

5 Claims, 7 Drawing Sheets

DIAGNOSTIC DEVICE AND METHOD

This application is a national phase filing of our International patent application with the serial number PCT/US04/01982, filed Jan. 22, 2004, which claims priority to now abandoned U.S. patent application with the Ser. No. 10/371,837, which was filed 20 Feb. 2003, which is a continuation-in-part of U.S. Pat. No. 6,821,790, which was filed Sep. 7, 2001 with the Ser. No. 09/949,314, which is a continuation-in-part of U.S. Pat. No. 6,291,249, which was filed Feb. 28, 2000 with the Ser. No. 09/514,686, which is a continuation-in-part of abandoned U.S. patent application Ser. No. 09/261,068 filed Mar. 2, 1999, all of which are incorporated herein by reference herein.

FIELD OF THE INVENTION

The field of the invention is clinical diagnostics and biotechnology.

BACKGROUND OF THE INVENTION

In vitro diagnostic tests to identify and treat diseases have become common tools in hospitals, homes and physician's offices. Biological fluids such as blood, urine or cerebrospinal fluids, which may at times contain blood, are the most frequently employed biological samples for such tests.

Blood contains many different components, some of which are present in strikingly varied concentrations from sample to sample. The percentages of both red and white blood cells in whole blood, for example, can vary among normal individuals, and even in the same individual over time, and in particular under pathological conditions. This large variation coupled with other factors such as storage conditions, coagulation, and the fragility of red blood cells, produces considerable technical problems in performing diagnostics using blood-containing samples.

Whole blood is usually separated into various fractions prior to testing. Among other things, separation into fractions can advantageously compensate for differences in hematocrit values, and in other ways reduce potential interference in up stream or down stream biochemical assays. Frequently employed fractions are serum, plasma, white cells, red blood cells and platelets. The terms "plasma" and "serum" are used herein to mean any fluid derived from whole blood from which a substantial portion of the cellular components has been removed. Plasma and serum are used herein interchangeably, because the presence or absence of coagulants is not a critical factor.

Blood separation technologies can be conceptually grouped into three categories—centrifugation, filtration, and solid-phase separation.

Centrifugation

Blood separation is routinely achieved by centrifugation. Centrifugation is generally desirable because: (1) centrifugation can generally separate cellular components from serum or plasma at an efficiency of greater than 95%; (2) centrifuges do not require highly trained personnel to operate; and (3) centrifugation allows concurrent processing of multiple samples in under 15 minutes. Centrifugation of blood is, however, also problematic. For example, centrifuges are expensive, involve multiple steps, are often unavailable at points of care such as bedside, schools or at home, and usually require electrical power for operation.

Filtration

Many filtration techniques are known for separating various components from blood. U.S. Pat. No. 4,987,085 to Allen et al., for example, describes a filtering system with descending pore size using a combination of glass fiber membranes and cellulose membranes. U.S. Pat. No. 4,753,776 to Hillman et al. discloses a glass microfiber filter using capillary force to retard the flow of cells. U.S. Pat. No. 4,256,693 to Kondo et al. discloses a multilayered chemical analysis element with filter layers made from at least one component selected from paper, nonwoven fabric, sheet-like filter material composed of powders or fibers such as man-made fibers or glass fibers. U.S. Pat. Nos. 3,663,374 and 4,246,693 disclose membrane filters for separating plasma from whole blood and U.S. Pat. Nos. 3,092,465, 3,630,957, 3,663,374, 4,246,693, 4,246,107, 2;330,410 disclose further filtration systems, some of which make use of small-pore membranes.

Known filtration techniques generally reduce the volume of blood required to only a few drops. Many filtration tests therefore contemplate using only about 25 to 75 µl of whole blood. Some filtration techniques have even been developed that require only about 5 to 50 µl of whole blood. In most applications, filtration occurs directly on a test-strip in which the filtration surface is placed above the reaction zone or zones of the strip. Filtration in these formats also reduces or eliminates the availability problems associated with centrifuges.

But these advances often create entirely new problems. For example, filters tend to retain significant amounts of plasma, and analytes present in low concentrations are frequently difficult to detect in the serum derived from small volumes of blood. Existing filters also tend to clog, and have undesirably slow flow rates. Agglutinating agents are often mixed with whole blood to reduce clogging and to improve flow rates, (see U.S. Pat. Nos. 5,262,067, 5,766,552, 5,660,798 and 5,652,148), but these problems remain.

Efforts have been made to improve the flow rate by modifying the force employed against the filter. But choices here are fairly limited. Filters are relatively simple to produce and use, but tend to cause excessive hemolysis of red blood cells. Capillary action, a phenomenon in which water or liquid will rise above normal liquid level as a result of attraction of molecules in liquid for each other and for the walls of a capillary can also be used. Capillary action, however, is generally too weak to effect rapid separation of large volumes. (See, for example, U.S. Pat. Nos. 5,660,798, 5,652,148 and 5,262,067). Moreover, separation of plasma by capillary action tends to retain a relatively large amount of fluid within the wicking membrane, or a collection membrane. This in turn may necessitate testing the wicking membrane or the collection membrane or both, or eluting the retained material from the membranes.

Solid-Phase Separation

Solid-phase separation typically involves a surface having binding to a target, the surface acting to immobilize and remove the target from a sample. Exemplary solid-phase separation techniques are binding chromatography, binding separation using beads, and hollow fibers separations.

One particularly advantageous type of solid-phase separation is magnetic separation, in which a target is captured by magnetically attractable (paramagnetic) beads. Since no physical barriers are present, as would be the case with filtration separation, magnetic separation tends to be relatively gentle. In U.S. Pat. No. 5,514,340 to Lansdorp and U.S. Pat. No. 5,123,901 to Carew, for example, magnetic wires are employed in batch processes to separate magnetic particles from a fluid. In U.S. Pat. No. 4,663,029 to Kelland et al. and U.S. Pat. No. 5,795,470 to Wang, magnetic particles are separated out from a fluid in a continuous flow process. Still other methods published for example in U.S. Pat. No. 5,536,475 to Moubayed, employ rocking separation chambers and multiple magnets to separate magnetic particles from a fluid.

One of the major limitations of applying known magnetic separation to blood separation is that multiple anti-ligands are required to remove all of the various types of cells and subcellular particles. Red blood cells, lymphocytes, monocytes, and platelets, for example, have different surface antigens, and do not specifically bind to any one antibody. Furthermore, lack or absence of ligands on the cells due to pathological conditions, genetic diseases or genetic variations or life cycle of cells generally reduce the efficiency with which the anti-ligands bind with the target cells.

The problems with known magnetic separation devices are exacerbated with increasing sample volumes, especially sample volumes over one milliliter. Since many diagnostic applications require serum volumes of up to one milliliter to satisfy the requirements of multiple tests or batteries of tests, magnetic separation has not been particularly useful. Moreover, assays such as glucose or hemoglobin tests are highly susceptible to interference caused by biological or chemical substances in the sample, including proteins, bilirubin, and drugs.

Thus, there is still a need to provide improved methods and apparatus for separating blood into its constituent parts, and especially for separating plasma or serum from whole blood.

SUMMARY OF THE INVENTION

In accordance with the present invention, a cell-containing sample is separated into a cell-containing portion and a substantially cell-depleted portion, by mixing the sample with both an additive and particles to produce a cell-containing network, and separating the network from the remaining substantially cell-depleted portion using a magnetic force.

In one aspect of preferred embodiments the vessel has a plurality of confining walls, and at least one of the confining walls is flexible. The sample is retained within the confining walls, preferably comprises whole blood, and the cell-containing portion largely comprises a network of inter-linked red blood cells, stem cells, leukocytes, or lymphocytes. Especially preferred linkers include anti-ligands such as primary antibodies that bind to a ligand or an antigen on or in the cell membranes of the cells to be isolated/separated, and secondary antibodies that bind to the primary antibodies. In another aspect of preferred embodiments, the primary antibodies are added directly to the sample, and the secondary antibodies are coupled to the surfaces of paramagnetic beads.

In another aspect of preferred embodiments, polymeric materials such as Polybrene®, cationic liposomes, cationic lipids, and polydendromers may be used in combination with anti-ligand(s) and magnetic separation or in combination with anti-ligand(s) and filtration. Aptamers can be used as anti-ligand(s) by themselves or in combination with cationic polymers, cationic liposomes, and dendromers.

In yet another aspect of preferred embodiments, the separation takes place within the confining walls, and while in some embodiments the separation employs at least in part a magnetic force, in other embodiments at least two forces are employed to separate the network from the substantially cell-depleted portion. Where two forces are employed for separation, one force is a magnetic force and another force is an electromechanical force transmitted through at least one confining wall, wherein the terms "electro-mechanical", "automatic", "hydraulic" and "pneumatic" are used interchangeably herein.

Various objects, features, aspects and advantages of the present invention will become more apparent from the following detailed description of preferred embodiments of the invention, along with the accompanying drawings in which like numerals represent like components.

DETAILED DESCRIPTION OF SPECIFIC EMBODIMENTS

Figure 1A:
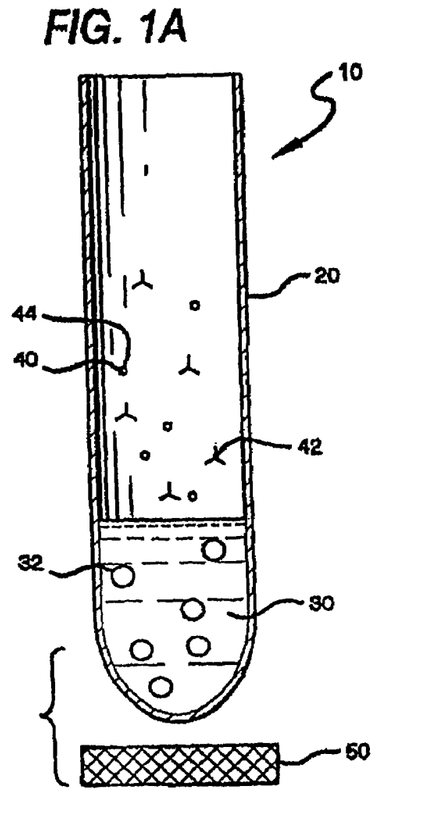
FIG. 1A is a schematic of a preferred embodiment in which separating agents are being added to a blood sample.

In the generalized preferred embodiment of FIG. 1A, a blood separation apparatus 10 comprises a vessel 20 and a magnet 50. The vessel 20 contains blood 30, to which is being added primary antibodies 42 having a substantial binding to cells, and particles 40 coated with a secondary antibody having a substantial binding to primary antibodies 42.

Vessel 20 is preferably an ordinary test tube or test tube-like vessel such as a vacutainer or falcon tube. The volume of such tubes is preferably less than about 10 ml, although it is contemplated that appropriate vessels may define sample cavities of greater or lesser volumes.

Although vessel 20 is depicted as having a typical test-tube shape, alternative vessels are contemplated to have different shapes. Thus, suitable vessels may have a narrowed top portion to facilitate recovery of the substantially red blood cell-depleted portion. Alternative vessels may also have differently shaped bottoms, such as a V-shaped or a flat bottom. In yet another example, an individual vessel may be formed as part of an array, such as in a multi-well microtiter plate. Further examples of suitable vessels include, hollow fibers, arrays of capillaries, beakers, pouches, dishes and cylinders—generally any device that can retain fluid within confining walls, and provide at least one opening. Appropriate vessels are even contemplated to include "open walled" structures such as a microscope slide having microchannels etched on glass or plastic, or a simple plastic foil or film.

It is specifically contemplated that vessels employed in conjunction with the teachings herein retain a sample within a plurality of confining walls, and that at least one of the confining walls is flexible. The term "flexible" confining wall as used herein refers to a wall that can be substantially deformed employing moderate pressure (i.e., less than 0.5 psi) without breaking or otherwise damaging the confining wall. For example, a plastic foil or thin latex sheet are considered flexible. In contrast, a typical thin (2 mm) polycarbonate plate would not be considered flexible under the scope of this definition, because polycarbonate plates can typically not be substantially deformed without breaking. Particularly contemplated vessels may therefore have one relatively rigid wall onto which at least one other confining flexible wall with individual compartments is mounted (e.g., a thin plastic sheet by heat sealing), and in even more particularly contemplated vessels, all of the confining walls may be flexible. Such vessels may have envelope shape and examples of contemplated vessels are described in U.S. patent application Ser. No. 09/272,234, issued as U.S. Pat. No. 6,300,138, which is incorporated herein by reference.

It is contemplated that vessels can be made from any appropriate material or materials, including glass, synthetic polymers, ceramics, metals, or mixtures thereof. Such vessel can be colored or transparent, translucent or non-translucent, and may or may not have graduation or other markings.

In FIG. 1A the sample being separated is whole blood. Such blood is generally contemplated to be fresh human whole blood, a few milliliters of which are preferably obtained by venipuncture. Another example is capillary blood, which can be obtained in volumes ranging from less than 10 to hundreds of μLs by use of a lancet. Furthermore, it is contemplated that sample volumes higher than a few microliters to a few milliliters can be used, especially where a relatively high number of cells is desired. For example, where lymphocytes are separated for use in a post-radiation transfusion in a cancer patient, suitable sample volumes may be substantially higher than a few milliliters. Similarly, where stem cells for organ regeneration are separated, the sample volume will likely exceed 50 ml and more. Therefore, contemplated volumes will typically be in the range of about 1-10 mL, more typically in the range of 10-100 mL, and most typically in the range of about 100-500 mL (and even more).

The blood can be pre-treated, such as by addition of an additive, or removal of a component. Contemplated additives include buffer, water or isotonic solution, anticoagulants, antibodies, and test solutions. Contemplated substances or components that can be removed include antibodies, globulins, albumin, and cellular fractions such as platelets, white blood cells etc.

The blood can also be derived from non-human sources, including vertebrate or invertebrate animals. Blood employed as set forth herein can also be taken from any type of storage, and as such may be cooled blood, frozen blood, or blood with preservatives.

In preferred embodiments, the primary antibodies 42 are mouse derived monoclonal antibodies to human red blood cells, which in the field would often be referred to as monoclonal Ab to hRBCs. The secondary antibodies 44 are preferably sheep, donkey, goat, or mouse derived anti-mouse IgG antibodies.

Techniques for raising the antibodies are well known. For example, both the primary and secondary antibodies can be derived from any appropriate source including, goat, sheep, horse or recombinant sources. Suitable antibodies can also be selected from many classes and subclasses, including IgG and IgM, and subclasses. Furthermore, antibodies can be selected from numerous molecular varieties, including proteolytic fragments or engineered fragments such as Fab or (Fab)$_2$, or chimeric antibodies. Combinations of antibodies are specifically contemplated.

Of course, both primary and secondary antibodies would advantageously have substantial binding to their respective targets. The primary antibodies would preferably have substantial binding to red blood cells, and in particular would have substantial binding to at least one ligand or component present on a surface of the red blood cells. The secondary antibodies would preferably have substantial binding to at least some component of the primary antibodies.

The secondary antibodies 44 are preferably included in the coating of coated particles 40. Such particles are attractable by magnetic force, and preferably comprise a paramagnetic composition embedded in synthetic polymers or cellulose. Although paramagnetic particles are preferred, the coated particles can also or alternatively include ferromagnetic or chromium material or mixtures thereof. In still further variations, suitable particles can be coated with many other materials including natural or synthetic polymers, agarose etc. The preferred particle size is in the range of 0.1-100 μm, but alternative sizes between 10-100 nm or larger than 100 μm are also contemplated. Viewed from another aspect, it is contemplated to employ particles having a mean volume between about $5 \times 10^{-24}$ m$^3$ and about $5 \times 10^{-6}$ m$^3$. Where red blood cells are being targeted, the diameter of the red cells may advantageously be about five times the diameter of the coated particles.

The term "coated" is used herein to mean any complete or partial covering of any exposed surface. In FIG. 1, the particles 40 are coated with a material that immobilizes the secondary antibodies. Such immobilization can be temporary or permanent, and can involve covalent or non-covalent binding. For example, non-covalent binding may involve incubating antibodies with the bead or other solid-pbase. As another example, covalent coupling of antibodies to a solid-phase may involve including reacting amino groups of an antibody with aldehydes on the solid-phase, or activated carboxyl groups on the solid-phase, resulting in a covalent bond.

In yet other embodiments, one or both of the primary and secondary antibodies can be replaced by or complimented with an alternative composition have the desired binding, and at least a minimally acceptable specificity. Anti-ligands are a general class of such alternative compositions, and are defined herein as any molecule that binds non-covalently to an appropriate ligand. Examples of anti-ligands and ligands include and are not limited to antibodies and antigens, respectively, and sense and anti-sense oligonucleotides in nucleic acids. Other polymers are contemplated as well as nucleotides. Additional examples are aptamers and lectins having a substantial binding to ligands.

The term "a cell-containing network" refers herein to an aggregate of at least more than one cell, from which individual cells cannot readily be mechanically removed without lysing the removed cells. Normally clotted blood is one example of a cell-containing network, but aggregates formed substantially by any combination mediated by molecular interactions such as hydrophobic-, hydrophilic-, electrostatic-, van-der-Waals-, ionic interaction or other molecular interactions are also contemplated. Thus, other examples of cell-containing networks are aggregates of red, white or other cells formed by combinations with antibodies or other linking agents having substantial binding to the cells. It is especially contemplated that such networks may include solid supports such as beads.

It is especially contemplated that heterogeneous aggregates can be formed using a mixture of red blood cells with two different antibodies, wherein the primary antibody binds the red blood cells, and the secondary antibody binds to the primary antibody. If only one of the two binding portions of the antibody is involved in such binding, the following aggregates can be formed: (a) primary antibody bound to a red blood cell; (b) secondary antibody bound to the a primary antibody only; and (c) secondary antibody bound to primary antibody that is. bound to a red blood cell or some other cell type in blood or body fluids. If both of the two binding portions of the antibodies are involved in binding, any combination of the aggregates (a), (b), (c) may be formed, thereby producing a potentially vast network of aggregates.

The sample, antibodies or other anti-ligands, and beads or other particles may be combined in the vessel in any order. For example, in one class of embodiments (not shown), vessels are contemplated to be pre-loaded with magnetically attractable beads. Suitable such vessels are commercially available as MiniMACS™ separation columns from Miltenyi Biotec™, and the columns are even provided with a separation enhancing device. The standard protocol would need to be modified to conform to the teachings herein, such as by pre-coating the beads with an appropriate anti-ligand, and by adding an appropriate anti-ligand to the sample.

The magnet 50 is generally a disc magnet, but in alternative embodiments the magnet can also have different shapes and designs. Contemplated alternative magnets include bar magnets, horseshoe magnets, ring magnets, and can have any suitable multiple pole geometry including quadrupoles, hexapoles and octapoles, etc. Magnets can be of the permanent type, electromagnets, or even super-conducting magnets, and may comprise ferromagnetic or rare earth magnets. Furthermore, the magnet need not be a single magnet, but can advantageously comprise a plurality of magnets. Preferred magnets have strengths in the range of 0 to 2 Tesla for permanent magnets, or 0-100 Tesla for electromagnets. Especially preferred magnets employ a permanent magnet of field strength 0 to 1 Tesla.

In further alternative aspects of the inventive subject matter, the sample is retained within a plurality of confining walls, and the separation takes place within the plurality of confining walls employing a first and a second force. While the first force comprises a magnetic force (vide supra), the second force comprises an automatic mechanical force that is transmitted through at least one of the confining walls. As used herein, the term "automatic" mechanical force is used herein to refer to a process in which a mechanical force is applied in a manner other than manually applying a force. In particularly contemplated embodiments, the automatic mechanical force comprises a pressure that is applied to a flexible confining wall. For example, in a vessel wherein all of the confining walls are flexible, a magnetic force may retain the network within the confining walls, while a mechanical force (e.g., one or more actuators compressing the vessel) assist in separation of the network from the substantially cell-depleted portion.

Figure 1B:
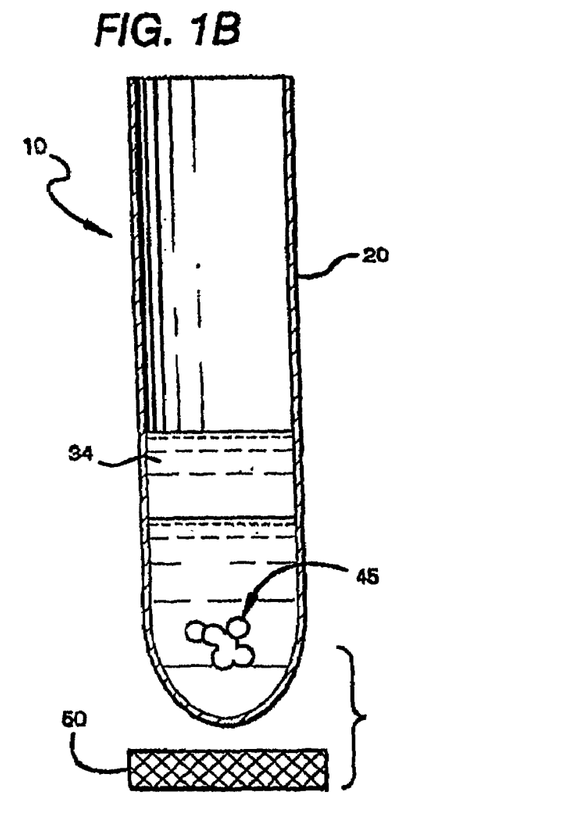
FIG. 1B is a schematic of the embodiment of FIG. 1A following separation of red blood cells.

In FIG. 1B several networks 45 have been formed from the blood cells 32 (not shown in detail), antibody coated paramagnetic particles 40 (not shown in detail), and anti-red blood cell antibodies 42 (not shown in detail). The particles 40 within the network 45 are being attracted by magnet 50, thereby separating out the cell-containing networks 45 from the substantially cell-depleted plasma 34.

Red blood cells 32 are generally mature non-nucleated erythrocytes. These blood cells usually are the predominant form of red blood cells present in a sample. In alternative embodiments, red blood cells can also be red blood cells carrying any type of hemoglobin including α, β, γ or fetal hemoglobin. The red blood cells can also be regular healthy blood cells or red blood cells giving raise to diseases e.g. sickle cell anemia or thalassemia. Appropriate red blood cells can also be in many stages of development, e.g. nucleated erythroblasts or aged, non-nucleated erythrocytes.

The inventive subject matter is, of course, not limited to mature non-nucleated erytlhrocytes, and specifically contemplates other stages of red cell development, other cells including white cells, and even cellular fragments including platelets. Thus, for example, where the sample comprises urine, a clinician or other individual may employ the inventive methods and apparatus to separate out bacterial cells or sloughed off bladder or urethral cells, and in such instances the red cells 32 of FIG. 1B may be replaced with non-erythrocytes.

Alternatively, various non-red blood cells may of particular interest, especially where such cells are separated for further clinical, experimental, or diagnostic use. Among particularly contemplated alternative non-red blood cells, various stem cells, lymphocytes, and leukocytes are especially preferred. The term "stem cell" as used herein refers to a cell that gives rise to a lineage of cells, and that may be characterized as a cell that upon division, produces dissimilar daughters, one replacing the original stem cell, the other differentiating further. While it is generally preferred that contemplated stem cells are undifferentiated stem cells, partially differentiated stem cells are also contemplated. Thus, suitable stem cells include embryonic stem cells, umbilical cord blood stem cells, and adult/peripheral stem cells. Consequently, the source of contemplated samples for use herein may vary considerably and may include blood, tissue samples (e.g., skin), commercially available stem cells and stem cell lines, and embryonic tissue. It is further contemplated that stem cells isolated by contemplated methods may be useful in a variety of clinical and research settings, and particularly preferred uses include at least partial regeneration of diseased or necrotic organs or organ substructures, research into differentiation signals and pathways, etc.

Where isolated non-red blood cells are leukocytes, all subtypes of white blood cells are generally contemplated suitable and include neutrophiles (polymorphs), lymphocytes, eosinophiles, and basophiles. Of particular interest are lymphocytes (i.e., white cells of the blood that are derived from stem cells of the lymphoid series), and especially various B cells, T cells, T helper cells, and memory B cells. Such cells may be obtained from numerous sources, however, it is generally contemplated that the most common source are blood, amniotic fluid, and bone marrow aspirate. Thus, it is contemplated that leukocytes or lymphocytes may be obtained from any appropriate source (typically, the sample is taken from a mammal, and more preferably, from a human).

It is further contemplated that all markers that can both (i) form a specific interaction for a desired cell type and (ii) allow a specific interaction with a high affinity binding partner can generally be used for separation of the desired cell type. As used herein, the term "high affinity binding partner" refers to an affinity of $K_d < 10^{-4}$ $mol^{-1}$. Consequently, numerous markers other than red blood cell markers (e.g., glycophorin A) are suitable for use herein, and an exemplary collection of suitable markers for various stem cells, leukocytes, and lymphocytes for use in separation is provided in Table 1, below.

| Marker | Synonyms | Specificity |
|---|---|---|
| Leukocyte Markers (general) | | |
| CD 1 | | Thymocytes, Langerhans histiocytes |
| CD 33 | | Myeloid progenitor and monocytes |

-continued

| Marker | Synonyms | Specificity |
| --- | --- | --- |
| S100 | | Interdigitating dendritic cells of the lymph node paracortex. |
| CD 45 | LCA, leukocyte common antigen | All leukocytes |
| CD 30 | Ki-I | Activation marker for B, T, and monocytes |
| T-Cell markers | | |
| CD 2 | | T and NK cells |
| CD 3 | | All thymocytes, T and NK cells |
| CD 4 | | Helper T cells |
| CD 5 | | All T cells, some B cells |
| CD 7 | | All T cells, some myeloid cells |
| CD 8 | | Cytotoxic T cells |
| CD 16 | | NK cells and granulocytes |
| B-Cell markers | | |
| CD 10 | CALLA Common acute lymphocytic leukemia antigen | Early precursor and pre-B cells |
| CD 19 | | preB, B cells, but not plasma cells |
| CD 20 | L26 | preB, but not plasma cells |
| CD 21 | EBV-R | Mature B and follicular dendritic cells |
| CD 22 | | Mature B |
| CD 23 | | Activated marrow B |
| Other specific and general markers | | |
| CD 15 | Leu M2 | All granulocytes, Reed Sternberg cells |
| CD 34 | | Early pluripotent progenitor cell |
| CD 61 | platelet glycophorin | Associated with M7 AML |
| EMA | epithelial marker antigen | Epithelial cells |
| TdT | | T and B lymphocytes, lost before maturity |
| Stem Cell Markers | | |
| SSEA-3 | | Primate embryonic stem cells |
| SSEA-4 | | Primate embryonic stem cells |
| TRA-1-60 | | Primate embryonic stem cells |
| TRA-1-81 | | Primate embryonic stem cells |
| Sca-1/ Thy-1.1 lo | | Hematopoietic stem cells |
| | | Hematopoietic stem cells |

Where a particular antibody or affinity reagent for a marker for a desired stem cell, leukocyte, or lymphocyte is not commercially available, it is contemplated that suitable antibodies or antibody fragments may be raised using standard procedures well known in the art (see e.g., Monoclonal Antibody Protocols (Methods in Molecular Biology, 45) by William C. Davis; Humana Press; ISBN: 0896033082).

It should still further be appreciated that cells bound to the high affinity binding partner (e.g., antibody or antibody fragment) can be released from such binding partners using a variety of techniques well known in the art, and particularly contemplated methods of release include competition with excess of antigen or epitope to which the high affinity binding partner is specific, high temperature treatment, acidification (e.g., pH<3.5), proteolysis, and mild chaotropic agents. Where it is desirable that an isolated cell is removed from the magnetic bead without separation of the high affinity binding partner from the cell, various methods of breaking a covalent bond between a high affinity binding partner and a magnetic particle are contemplated. Among such methods, reductive cleavage of a disulfide bond, or enzymatic cleavage (e.g., via an peptidase) of a bond in a linker connecting the high affinity binding partner to the magnetic particle are particularly preferred. Exemplary methods of removing a hapten from an antibody are described in Affinity Chromatography: Methods and Protocols (Methods in Molecular Biology) by Pascal Bailon, George K. Ehrlich, Wen-Jian Fung, wo Berthold, Wolfgang Berthold (Humana Press; ISBN: 0896036944), or in Handbook of Afinity Chromatography by Toni Kline (Marcel Dekker; ISBN: 0824789393).

In addition to operating on a wide variety of samples, it is also contemplated that the inventive methods and apparatus described herein can be employed to measure a wide variety of analytes. Contemplated analytes include tumor markers such as prostate specific antigen (PSA), infectious disease markers, endocrine markers such as testosterone, estrogen, progesterone and various cytokines, and metabolic markers such as creatinine, glucose.

Figure 2A:
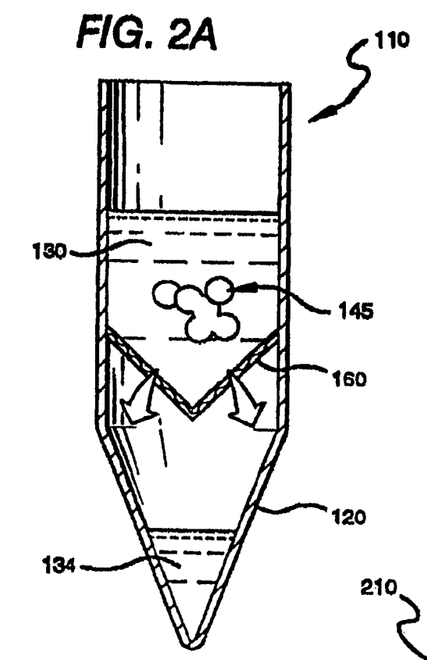
FIG. 2A is a schematic of an alternative embodiment.

In FIG. 2A a blood separation apparatus 110 has a soft-walled or otherwise flexible vessel 120 containing a network 145 formed from whole blood 130 comprising red blood cells 132 (not shown in detail), anti-red blood cell antibodies 142 (not shown in detail) and anti-mouse antibodies 144 (not shown in detail). A filter 160 filters out the network 145, and allows plasma 134 to pass through to a collection area.

The filter 160 is preferably a glass fiber filter having a pore size below the size of the cellular components of blood or larger than the individual cells, but smaller than the network. In alternative embodiments the filter can be made from many materials including chromatographic paper natural or synthetic fibers, porous membranes etc. Examples for those alternative filters are nylon fiber filters, size exclusion membranes, paper filters, woven fabric filters. Furthermore, the filters may or may not be coated with material e.g. to reduce hemolysis or to specifically retain selected fractions or molecules. Appropriate coatings include polyvinylalcohol, polyvinylacetate, polycationic polymers, lectins or antibodies.

In FIG. 2A the filtrate portion of the sample is passed through the filter by gravity. However, it is recognized that the driving force to move the sample through the filter can be a force or pressure differential across the membrane, and can be achieved in many ways including centrifugation, vacuum, compressed gas, or a magnet as described elsewhere herein. The filtration time can vary greatly, but is generally considered to be within the range of a few seconds to less than 30 min. Of course it should be appreciated that such separation characteristics and efficiency may also be obtained from various cells, other than red blood cells, including for example, leukocytes, lymphocytes, and stem cells.

Figure 2B:
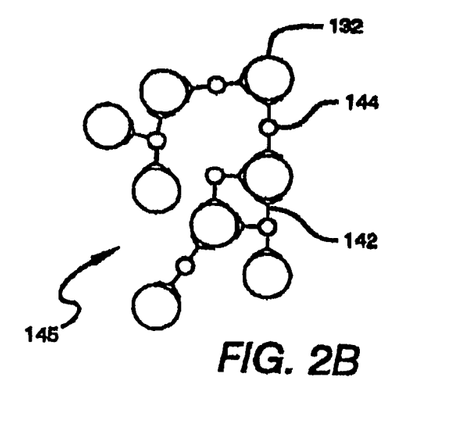
FIG. 2B is a schematic of binding interactions contemplated to be present in the embodiment of FIG. 2A.

FIG. 2B depicts details of a possible portion of network 145, which includes anti-red blood cell antibodies 142 bound to red blood cells 132, and anti-mouse antibodies 144 bound to anti-red blood cell antibodies 142. Those skilled in the art will recognize that a single network can contain millions of cells, and it should be appreciated that the orientation and connections of the various components in FIG. 2B are purely exemplary, and would not necessarily ever be found in an actual network. Among other things, a real-life network would be three-dimensional, rather than the two dimensional schematic as shown, and the antibodies would be much smaller than that shown in the drawing. It should also be appreciated that network 45 of FIG. 1B is contemplated to have corresponding structures to that depicted in FIG. 2B.

Figure 3:
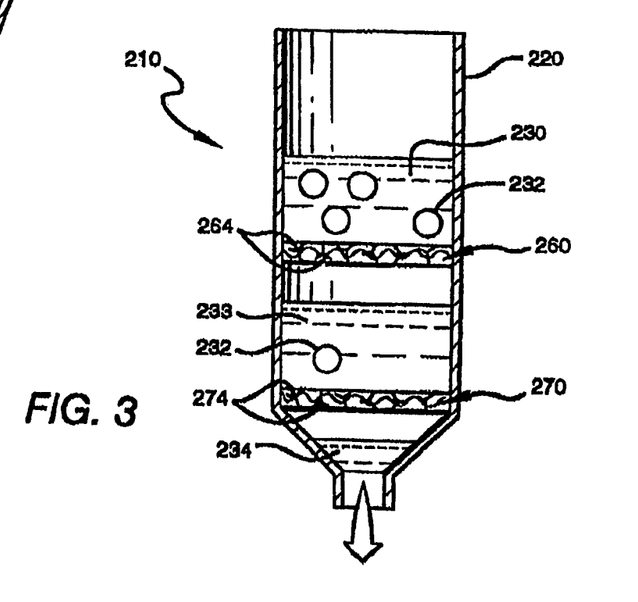
FIG. 3 is a schematic of another alternative embodiment.

In FIG. 3 a blood separation apparatus 210 has a vessel 220 that receives a blood sample 230, a pre-filter 260 coated with anti-red blood cell antibodies 264, and a secondary filter 270 coated with anti-red blood cell antibodies 274. A portion of the sample 230 has filtered through the pre-filter 260 to provide a partially cell-depleted fluid 233, and a portion of the cell-depleted fluid 233 has filtered through the secondary filter 270 to provide a substantially cell-depleted fluid 234.

Here, the vessel 220 is contemplated to be a vessel falling within bounds of vessels previously described with respect to vessel 20, and similar correspondences exist with respect to blood 230 and 30, red blood cells 232 and 32, primary antibodies 264 and 42, secondary antibodies 274 and 44, and plasma 234 and 34.

The preferred pre-filter material is nylon wool 260, comprising an uncompressed layer of nylon fibers. The secondary filter 270 is preferably a glass fiber disk onto which mouse anti-red blood cell antibodies 274 are bound. In alternative embodiments, either or both of the filters 260 and 270 can be substituted with any other suitable filter material including a fibrous filter material, filter paper, porous membranes etc. Examples hereof include coated or uncoated glass fibers, mineral wool, chromatographic paper etc. Furthermore, the filter material may or may not be coated e.g. to reduce hemolysis or to specifically retain selected fractions or molecules. Appropriate coatings include polyvinylalcohol, polyvinylacetate, polycationic polymers, lectins or antibodies other than that previously described.

Figure 4:
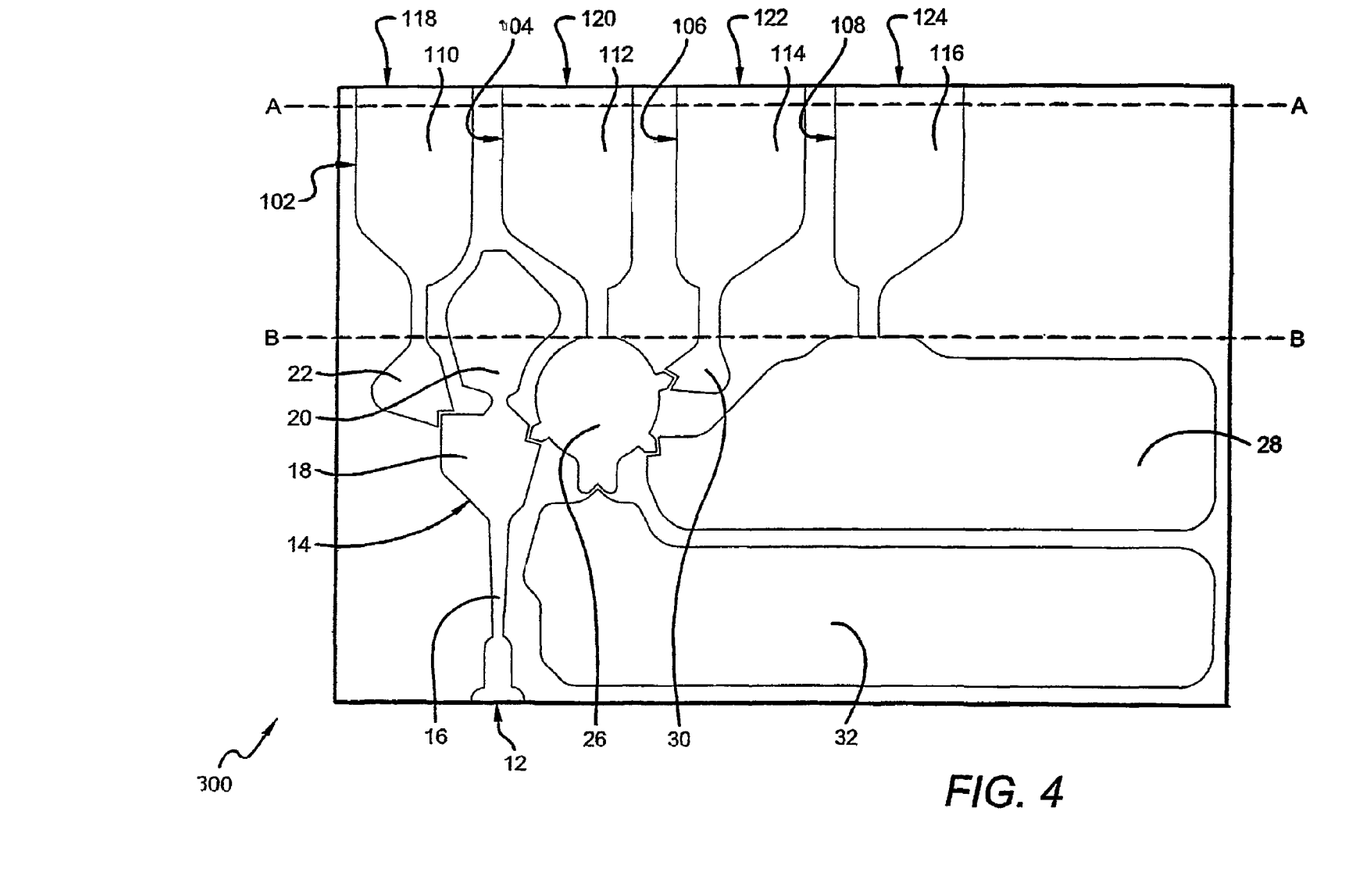
FIG. 4 is a plan view of an exemplary diagnostic container.

In FIG. 4, a plan view of an alternative and particularly preferred exemplary disposable diagnostic container 10 is shown and generally comprises a pouch having a sample inlet port 12, a plurality of compartments 13, 22, 26, 28, 30, and 32, as well as passageway 16 coupling the inlet port 12 with compartment 13, and portals 24, 34, 36, 38 and 40 interconnecting the various compartments.

Container 10 is a relatively flat, laminated plastic pouch measuring about 8.5 cm by about 19 cm, and about one millimeter thick, in which the compartments, inlet port, passageway and portals are all defined by heat sealing. The nature and dimensions of the container, arrangement of compartments and interconnections, as well as the contents of the compartments will, of course, vary from embodiment to embodiment, and those skilled in the art will recognize that the embodiment of FIG. 4 is merely exemplary of an enormous number of such possible containers.

The size of the container, for example, largely depends on the volume of reactants to be contained, although it is contemplated that practical containers will typically be sized to define a volume in the range of between 50 microliters and about 5 milliliters. Suitable containers may have many different shapes, so long as the shape permits contact of at least one side of the container with a plurality of actuators. Preferred shapes are flat, envelope-like shapes, but box-like, round, hemispherical, or even spherical shapes, are also contemplated.

The opposing top and bottom sheets forming container 10 may advantageously be formed from a thermoplastic material, including polypropylene, polyester, polyethylene, polyvinyl chloride, polyvinyl chloride, and polyurethane. Such sheets are contemplated to have a relatively uniform thickness between about 0.05 mm to about 2 mm. The opposing sheets need not be fabricated from the same materials. For example, one sheet may comprise a reflective foil, and the other sheet may comprise a transparent or translucent plastic. The use of foil can help promote temperature stability, and can serve as an additional moisture and oxygen barrier. Foil can also enhance thermal transfer from a heating source to a sample or reagent.

Preferred containers are flexible, either in whole or in part. Flexibility as characterized herein is the capability of yielding to a reasonable force by temporarily changing shape without damaging the structure or material. A reasonable force, as used herein, is a pressure, typically below 5 lb/in$^2$. For example, a preferred flat, envelope-like container is sufficiently flexible to be wrapped around an inch diameter cylindrical object without breaking or tearing the container. In another example, a portion of a container may advantageously be sufficiently flexible to displace a volume carried within that portion without rupturing the outer walls. Moreover, it is contemplated that at least part of the top and/or bottom sheets from which the container may be fabricated is transparent or translucent. The container may furthermore have a plurality of openings. The number of openings may vary considerably between at least one opening and twenty openings or more. Such openings may have a closing mechanism, be sealable or permanently open. Furthermore, some of the openings may be in liquid communication with each other, or may be used as a vent or an overflow. The container is furthermore characterized by having a plurality of compartments.

Container 10 also includes attachment holes 42 for mounting on alignment posts in an analyzer 400. Alternative attachment devices or methods are also contemplated, including hooks, loops and other mounting attachments coupled to the container 10 at appropriate locations. It is further contemplated that container. 10 may be devoid of mounting components.

One or more labels (not shown) may also be affixed to the container 10. Labels may indicate identification marks, information relating to the type of diagnostic test being conducted, as well as patient information, test result data, or other information. The label(s) may optionally be removable, and may, for example, be removed from the container 10 to be placed in a patient's medical file, thereby eliminating the need for transferring data with attendant possibility for error.

Inlet port 12 serves as an entry point for receiving samples or other materials. Many configurations are contemplated, although it is preferable that the entry point uses some sort of common connection mechanism. For example, the entry point 12 in FIG. 4 is a female portion of a Luer lock mechanism. Alternative entry ports may be either simpler or more complex, and may contain a padding that can be punctured or pierced using a needle. Contemplated entry points may also be placed elsewhere on a container other than as depicted in FIG. 4. For example, a suitable entry point for a solid material may be formed as a simple slot in one of the sheets forming the top or bottom of the container. Such an entry point may be well suited for receiving a relatively solid piece such as a tissue or mineral sample, and may be sealable by a flap or tape mechanism.

Compartments 13, 22, 26, 28, 30, and 32 are portions of container 10 that are fluidly separated from other portions of the container during at least some period of time. In general, compartments are separated from one another using at least one continuous element that contacts at least one of the walls of the container. For example, if the container is a cylinder, the continuous element could be a divider that is more or less perpendicular to the longitudinal axis of the cylinder, and contacts the inner circumference of the cylinder. Where the container is a flat bag, the continuous element may advantageously comprise a heat seal between opposing sides, in a form enclosing a defined space.

The volume of preferred compartments may advantageously vary between about 3% to approximately 90% of the total volume of the container. Such compartments may be filled with at sample, a reagent, or air, but the compartment may also have essentially no void volume. By way of example, compartment 22 may be designed to contain about 1 ml of a binding reactant, and wash compartment 28 may be designed to hold up to about 5 ml of a solvent solution.

At least some of the compartments may advantageously comprise a transparent portion through which a signal can be detected, or the progress of a reaction can be monitored. In such instances it may also be advantageous for an opposing surface to exhibit a reflective surface to improve signal detection. Compartments may also be shielded, for example against heat, light, or other radiation. Especially preferred signals that can be detected include signals from a luminescent and/or fluorescent marker, and scattered light (e.g., light scattered by cells or cellular debries).

Compartments may have one or more openings, such as those at portals 34, 36, 38, and 40. Such openings may be in permanent liquid communication with the rest of the container, for example, by an incomplete wall surrounding the compartment. Openings may also be temporarily closed. For example, a breakable seal may form the opening, which separates the compartment from the rest of the container, until an opening force breaks the seal. Typically, the breakable seal is a chevron break point allowing a fluid to pass under about 5-15 psi. In another example, the opening comprises a one-way valve, which permits only a unidirectional flow of material when a pressure difference is applied between the ends of the valve. In yet a further example, the opening may be temporarily closed by a closing force. Typically, the closing force is delivered via a compression pad from outside the container, which effects a temporary physical separation of the compartment from the rest of the container.

Figure 5:
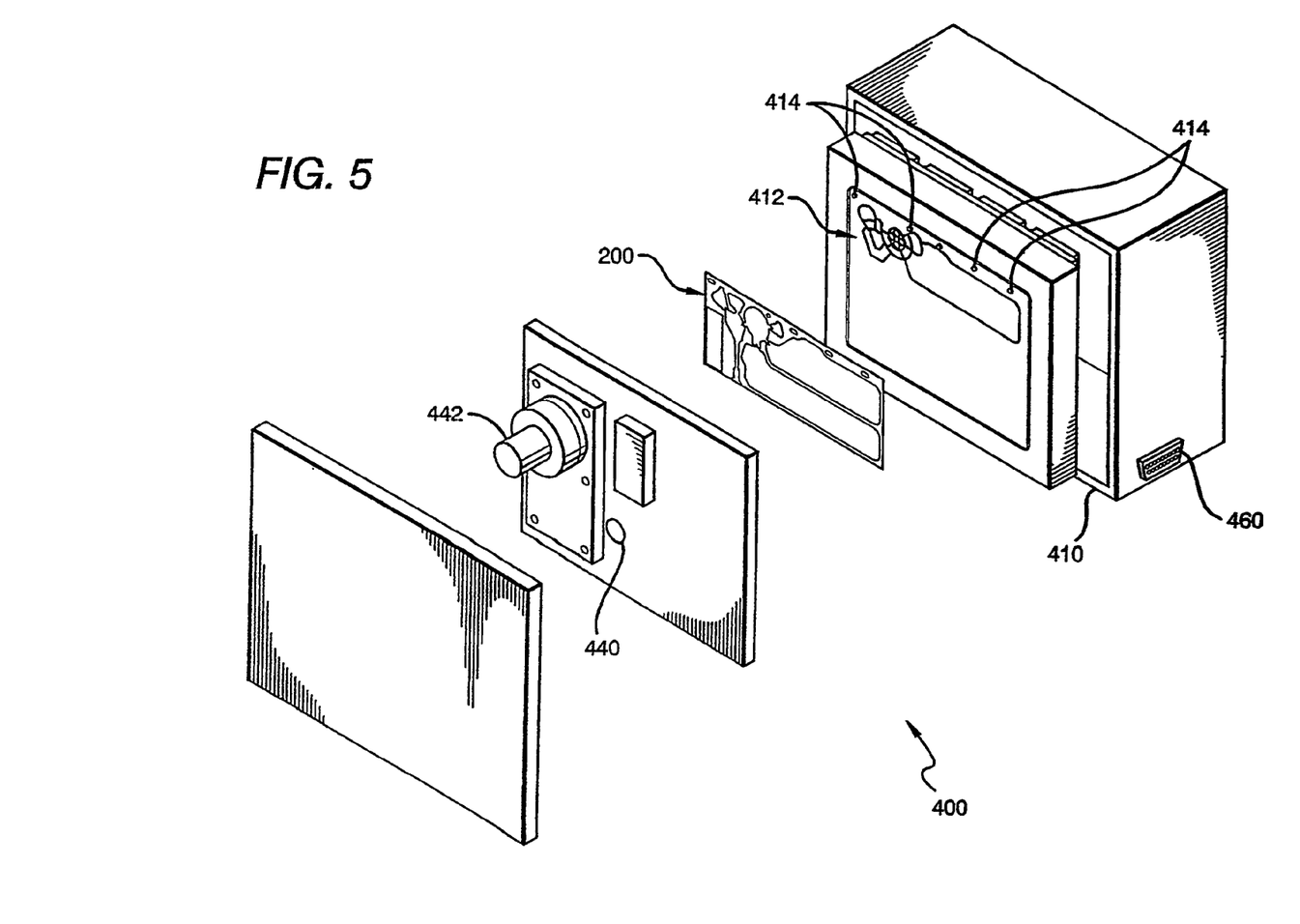
FIG. 5 is a perspective view of an exemplary analyzer for a diagnostic container of FIG. 4.

Passageway 16 and portals 34, 36, 38 and 40 serve to fluidly connect various compartments and other spaces within the container, and with the external environment. The term "fluidly connect" specifically includes movement of any fluidizable composition, whether a liquid, gas, or fluidized solid. In many instances the fluid will be intended to move in a single direction only, but in other instances it may be advantageous to move at least a portion of a fluid in both forward and backwards directions. In some cases compartments or other spaces may be separated by a barrier for a period of time, and it is contemplated that the barrier will at some point be breached. In such instances the separated compartments or other spaces are considered to be "fluidly connectable."

Where containers according to FIG. 4 are employed, it is especially preferred that such containers cooperate with an automated analyzer as schematically depicted in FIG. 5. Here, an analyzer 400 generally comprises a housing 410 having a container actuator assembly 412, a door 420, a detector 440, a scatter unit 450, and an interface 460. Analyzer 400 is shown with an exemplary work piece container 200. The housing 410 houses essentially all of the electronic or other circuitry needed to complete the contemplated tests. Of course, housing 410 can be designed using any suitable shape and dimensions, and can be formed from plastic, metal, or any other suitable materials. A container receiving zone with actuator assembly 412 cooperates with door 420 to receive container 10 during the contemplated testing. In alternative embodiments a door is not needed at all, and the container can instead be inserted into an access slot. Alignment posts 414 may be configured in any suitable fashion, and can be eliminated altogether.

Actuator assembly 412 is used to deliver one or more forces to the container 10, with the object of affecting some material with container 10. Examples of actuators that may form part of group 412 are compression pads, roll bars, or wheels. Contemplated actuators may also have one or more additional functions, including heating, cooling, illuminating, and delivering a magnetic force. For example, an actuator may heat inactivate an enzyme, or warm a reaction to a desired temperature. In another example, an actuator may be used to concentrate an analyte by binding it the surface of a magnetic bead. Actuators may also be employed to modify a volume occupied by fluids, solids, or air. The fluids may, for example, include a buffer, a sample, a reaction mixture, a reagent solution, etc. The solids may include paramagnetic beads, and the gases may include nitrogen or argon as protective agents, or $CO_2$ as a byproduct of a chemical reaction.

Where an actuator comprises a compression pad, the pad can be made from any material suitable for exerting an appropriate force to a portion of a container, in an appropriate pattern. Typically, a compression pad is a substantially flat surface, and has a shape corresponding to the shape of a compartment or passageway. Where an actuator is employed to otherwise seal a partition, a partitioning edge can be provided, preferably in the form of a wedge or a compression pad having a protrusion.

Furthermore, in an alternative aspect of the inventive subject matter, the actuator group may include one actuator (which may act as compression pad, heating pad, or serve other function) that includes a light source and/or a light detector (preferably, but not necessarily a detector other than the detector that detects an analyte signal). For example, it is contemplated that the actuator may include a laser diode (e.g., with wavelength of about 632 nm) and that the detector includes a photocell that is spaced apart from the laser diode such that the detector can detect light emitted by the laser diode that is scattered from the cells in a cell-containing sample.

Of course, it should be recognized that the location of the light source and/or the light detector need not be limited to a compression pad, and in a more preferred aspect, the light source and/or the light detector may be disposed in separate compression pads, or on opposite sides of the flat container, and in an even more preferred aspect, at least one of the light source and/or the light detector are located in the analytical device on the side opposite to the actuator group (i.e., the side or portion of the device that contacts the container, and that does not include the actuator group (e.g., the door, or adjacent to the signal detector)). For example, where a device comprises a light source and a light detector on the same side (relative to the container), the distance between the light source and the light detector is preferably between about 1 mm and 10 mm, and most typically about 3.5 mm. Alternatively, the function of the light detector may also be provided by the photomultiplier tube that is employed for detection of the analyte signal, and the distance between the light source and the photomultiplier may vary accordingly (e.g., typically between 1 mm and 10 mm).

Figure 6:
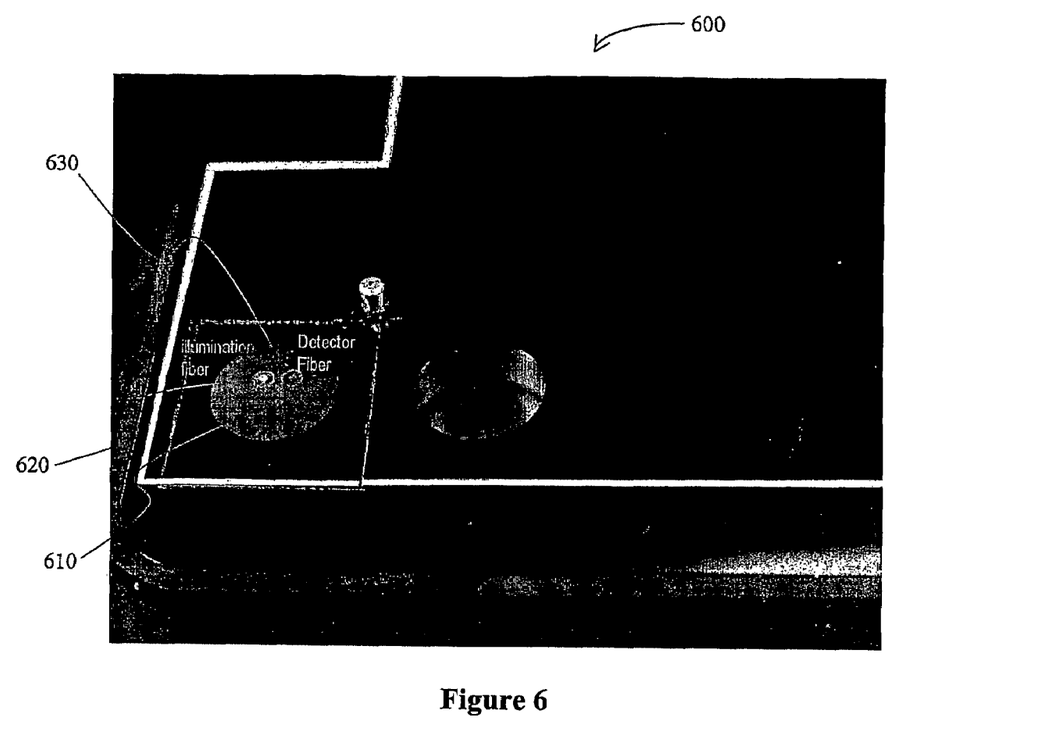
FIG. 6 is a photograph showing a detail view of an exemplary analyzer with an actuator comprising a light guide for illumination and reading of scattered light.

Moreover, it should be appreciated that the light source and/or the light detector may be replaced with a light guide (e.g., fiber optic cable, or other light transmitting structure), such that one end of the light guide is in optical communication with the cell-containing sample, and the other end of the light guide is in optical communication with the light source or the light detector. An exemplary detail view of two light guides an exemplary analyzer is shown in FIG. 6, wherein the analyzer 600 (only part shown in detail view) has a scatter unit 610 that includes a first light guide 620 (optically coupled to a light source) and a second light guide 630 (optically coupled to a photocell). Scatter unit 610 is proximal to a cavity that houses a photomultiplier tube.

In still further alternative aspects, it is contemplated that the light source and wavelength may vary considerably. For example, suitable light sources include numerous monochromatic and polychromatic light sources, and may provide incandescent, fluorescent, or laser light. Furthermore, where a particular wavelength is desired, one or more filters may be optically coupled to the light source and/or the light detector. In yet further alternative aspects, the nature of the light detector may vary considerably and the same considerations as described below for the detector 440 apply. Moreover, the inventors contemplate that the light detector may also be replaced by the detector 440 in FIG. 5.

Detector 440 is essentially one, or any combination of signal detectors used to detect a signal generated through use of the container. Contemplated signal detectors include a photomultiplier tube, a photodiode, and a charge-coupled device. It is optional to include detector 440 in analyzer 400. An optional printer 450 is used to print information on any combination of human or machine-readable formats, including printing on a paper label or sheet. It is optional to include a printer in analyzer 400. Interface 460 can be any type of electronic or other means of exchanging information with another device. A typical interface is a common RS232 (serial) data port. Not shown are other options for analyzer 400, including a scanner than can detect a bar code, or other hand or machine written information included on a label.

Depending on the wavelength of the light emitted by the light source, it should be recognized that numerous measurement functions other than light scatter to determine hematocrit may be employed. For example, it is especially preferred that (after hematocrit is determined and a cell-lysing agent is added to the blood sample), hemoglobin, and/or oxyhemoglobin may be spectrophotometrically determined in the sample container using the appropriate wavelength. There are numerous methods known in the art to determine hemoglobin content and all of the known methods are considered suitable for use herein. For example, Bull et al. describe a standard photometric procedure in "Reference and Selected Procedures for the Quantitative Determination of Hemoglobin in Blood; Approved Standard" (ISBN 1-56238-425-2), which is incorporated by reference herein.

It should be particularly appreciated that a combination of analytical methods using the light source and light detector (or photomultiplier) for a first analysis and the photomultiplier for a second analysis of the same sample may be especially advantageous where normalization of the second analysis result is desirable or indispensable. For example, glycosylated hemoglobin is frequently measured as a fraction of glycosylated hemoglobin over total hemoglobin. Therefore, determination of total hemoglobin in contemplated analytic devices may be performed in a spectrophotometric test using the light source and light detector of the scatter unit, while determination of glycosylated hemoglobin is performed in an immunoassay using the photomultiplier. Of course, it should be recognized that the particular nature of the first and second test is not limited to total hemoglobin and glycosylated hemoglobin. In fact, all known tests that require signal detection of two signals with different wavelength and of different origin are contemplated suitable for use herein. For example, the first signal may include an absorption, reflection, and/or scatter signal, while the second signal may be a bioluminescence signal, a chemiluminescence signal, a fluorescence signal, and/or a phosphorescence signal.

The analyzer can be programmable such that the compression pads and partitioning edges apply particular external force at particular times during the diagnostic test. In addition, the analyzer apparatus can have an alignment means (e.g., a plurality of pins) for proper positioning of the container in the device. Further, the analyzer can have pressure sensors on either side of each compression pad and partitioning edge. These sensors can be used to determine and regulate the amount of pressure being applied. In addition, these sensors can be used to determine whether each compression pad and partitioning edge is working properly during operation. Similarly, the light source and the light detector may be operated at various times to provide an operator and/or software light scatter information of a sample, and especially cell-containing sample.

In general, a sample is deposited into inlet port 12 under pressure, and travels to sample compartment 13. Excess sample beyond the capacity of compartment 13 spills over into a spillage compartment 20, which serves to aliquot the amount of sample in compartment 13. If the sample comprises a cell-containing fluid (e.g., straight or diluted whole blood, optionally admixed with one or more reagents), it is especially preferred that the light source emits a light into the sample (preferably with light having a maximum at a wavelength of between 620 nm-660 nm) thereby generating a scattered light, which is then detected by the light detector.

As a person of ordinary skill in the art will readily appreciate, the intensity of the so created scattered light in a cell-containing sample is dependent on the amount of hematocrit in the cell containing sample. The term "hematocrit" as used herein refers to the totality of cells and cellular debris in a blood sample and therefore includes erythrocytes, leukocytes, thrombocytes, etc. There are numerous methods known in the art to calculate the hematocrit value in a cell-containing sample, and especially in blood, and exemplary references for such determinations include U.S. Pat. Nos. 6,419,822 and 6,064,474, which are incorporated by reference herein.

A first reactant from compartment 22 is added to the sample, and after appropriate incubation the sample is shunted to reaction compartment 26. Reaction chamber 26 may contain additional reactants, and still further more reactants can be added from substrate or other reactant compartment 30. At one or more points in the processing stage the sample can be washed by a wash fluid from wash compartment 28. Waste material is forced into waste compartment 32. During these processes, various reactions take place with respect to an analyte within the sample, and a color or other detectable signal is produced that corresponds to the amount or existence of analyte. The signal is "read" through one of the side walls of compartment 26.

Where desirable, the read signal is then computed with the measured scattered light to normalize the read signal to a value that corresponds to a value of the sample from which the hematocrit has previously been removed. Therefore, it should be particularly appreciated that using contemplated configurations and methods, an analyte can be detected in a cell-containing sample (and preferably whole blood) without removing the cells from the sample.

EXPERIMENTS

Tests to separate red blood cells from plasma were performed, and the results are described below. Further tests were performed to determine levels of various antigens in cell-containing fluid without prior removal of cellular components from the fluid. These tests are only intended to be illustrative of some of the principles set forth above, and are not intended to be read as limitations on the scope of the claimed subject matter.

Experiment Set 1

In a first series of experiments, precipitation of red blood cells was performed using mouse anti-red blood cell antibodies, paramagnetic beads coated with goat anti-mouse antibodies and 0.5 ml of anti-coagulated whole blood. Heparinized, EDTA or citrated whole blood was mixed with 10 μl undiluted mouse anti-red blood cell antibody solution (Red Out™; Robbins Scientific Corp.) for 2 minutes; next 10 μl of a solution (isotonic PBS, pH 7.4) containing paramagnetic beads (Cortex Biochem Inc., MagaCell™ or MagaBeads™; 30 mg/mL; or Pierce MagnaBind™) coated with goat anti-mouse antibodies was added and mixed gently for 2 minutes. The bottom of the tube was placed on a magnet (permanent iron magnet; approximately 0.2 Tesla). Precipitation of the cellular network started instantly, and was substantially finished after about 2 minutes. Plasma was collected by aspiration from the top of the vessel.

Significantly, methods and apparatus described herein have been found to separate at least 70% (by volume) of the theoretically available cell-depleted portion from the network within a relatively short period of time. In many cases the time period for such 90% separation is less than 30 minutes, in other cases less than ten minutes, and in still other cases less than 2 minutes. Separations have also been performed using the methods described herein that achieve at least 80%, at least 90%, at least 95% and at least 98% of the theoretically available cell-depleted portion from the network within less than 30 minutes.

It should especially be appreciated that such separation characteristics and separation efficiencies may also be obtained using various cells other than red blood cells, and especially contemplated alternative cells include various stem cells, lymphocytes, and leukocytes.

Experiment Set 2

In a second series of experiments, precipitation of red blood cells on a microscope slide was performed using whole blood, mouse anti-red blood cell antibodies and paramagnetic beads coated with goat anti-mouse antibodies. To 0.2 ml fresh whole blood, 5:1 of an anti-red blood cell antibody containing solution (Red Out™) was added, mixed and incubated for 2 min at room temperature. Then, 5: L of a solution containing paramagnetic beads coated with goat anti-mouse antibodies (MagaCell™ or MagaBeads™ or MagaBind™) was added, mixed, and after another 2 minutes, two disk magnets were positioned at opposite ends of the slide. After about 1.5 minutes, a clear plasma containing zone was formed between the two magnets and this was retrieved with a pipette without disturbing the laterally-fixed cell-containing network.

Experiment Set 3

Flat envelopes sealed on three of four sides were prepared from transparency acetate sheets (for example, the 3M Inc. product, 3MCG3460), or plastic sheet protectors (e.g., Avery-Dennison PV119E), or from small "ZipLock" or ITW Inc. MiniGrip™ bags (2.5×3 cm: 2.0 mil). One-half to 1 mL of anti-coagulated whole blood was injected into the bag; 10 uL of Red Out™ (see above) was added and mixed with blood by gently rocking the container. After 2 minutes, the anti-mouse coated magnetic beads (MagaCell™) were added, mixed and the open side of the bag sealed. Two minutes later the bag was placed horizontally on a rectangular permanent iron magnet (approximately 0.2 Tesla). The magnetic particles and attached cellular networked moved adjacent to the magnet, leaving a clear layer of plasma as supernatant. The bag was then rotated into an upright position while still on the magnet, opened, and plasma aspirated using a pipette. It was also discovered that envelopes or bags (containing blood previously treated with anti-RBC antibodies and anti-mouse coated paramagnetic beads) could be passed between two permanent magnets separated a narrow distance. As the sack was drawn upward between magnets, the cellular network was pulled to the bottom of the container, producing an overlying layer of plasma.

Thus, in this example a vessel retains a sample within a plurality of flexible confining walls, and a cell-containing network formed within the sample is separated within the plurality of confining walls. Alternatively, instead of passing the envelopes or bags between two magnets, compression of the bag utilizing actuators or other mechanical devices could be employed to move the cellular network relative to the vessel. In this case, a second force (i.e., an automatic mechanical force) is employed to separate the network from the substantially cell-depleted portion, wherein the second force is transmitted through at least one of the confining walls.

Experiment Set 4

In one experiment, a small amount of steel wool (washed and treated with 5 mg/mL BSA in PBS for 12 hours) was added to the sample container prior to addition of blood and precipitating reagents. After addition of RedOut™ and MagaCell™ reagents (each for 2 minutes), the tube was placed on the magnet. The paramagnetic beads contained within the cellular network were immobilized to the steel wool. A pipette tip was used for aspiration of plasma that was essentially free of blood cells. When coated with protein or some other polymer, the steel wool caused very little hemolysis in the cellular pellet in a 2-hr period. It is further contemplated that iron wire, wool, or beads could be added as above if it were coated with other non-hemolyzing polymers such as dextran, polyvinylpyrilidone on polyethylene glycol etc.

In another experiment, 15 iron brads were taped around the external bottom ⅓ of a 12 mm glass tube in which whole blood was incubated as described above with mouse anti-red blood cell antibodies and paramagnetic beads coated with goat anti-mouse antibodies. Placing the tube on a rectangular magnet produced an almost immediate deposition on the bottom and sides of the tube. The external brads place the magnetic source closer to the sample tube, thus applying a relatively uniform source of secondary lateral attraction to the entire sample column and as the cellular network moves to the sides of the tube, it aggregates further.

Experiment Set 5

Test results produced in accordance with methods and apparatus described herein are depicted in Table 1. In this regard it should be noted that centrifugation is at least 99% effective in removing cellular matter from whole blood, (99% separation efficiency) and that methods and apparatus described herein (listed as "Device" in the table) are almost as effective. In particular, methods and apparatus described herein can be described as having separation efficiency of least 90%, at least 95%, and at least 98%.

TABLE 1

| Subject | Plasma Volume mL | | PSA Ng/mL | | Testosterone ng/mL | | Creatinine mg/dL | |
|---|---|---|---|---|---|---|---|---|
| | Centrifugation | Device | Centrifugation | Device | Centrifugation | Device | Centrifugation | Device |
| 1 | 0.45 | 0.36 | 28.5 | 27.2 | 4.78 | 5.45 | 0.75 | 0.64 |
| 2 | 0.55 | 0.48 | 25.1 | 23.2 | 14.45 | 11.2 | 0.70 | 0.62 |
| 3 | 0.53 | 0.48 | 27.2 | 26.4 | 16.19 | 15.18 | 1.04 | 1.06 |
| 4 | 0.48 | 0.40 | 26.9 | 24.8 | 11.18 | 10.96 | 0.97 | 0.91 |
| 5 | 0.57 | 0.51 | 25.9 | 24.2 | | | 0.84 | 0.91 |
| 6 | | | 21.3 | 20.2 | 10.97 | 10.15 | 1.11 | 1.10 |
| 7 | | | 25.2 | 23.6 | 6.08 | 7.58 | 0.69 | 0.72 |
| 8 | | | 25.5 | 20.4 | 18.06 | 22.79 | 0.99 | 0.91 |
| 9 | | | 16.4 | 16.6 | 0.46 | 0.27 | 1.35 | 1.49 |

| Subject | Hemoglobin g/dL | | Plasma Hematocrit % | | Red Blood Cells millions/uL | | White Blood Cells thousands/uL | |
|---|---|---|---|---|---|---|---|---|
| | Centrifugation | Device | Centrifugation | Device | Centrifugation | Device | Centrifugation | Device |
| 1 | 0.27 | 0.16 | | | | | | |
| 2 | 0.27 | 0.19 | | | | | | |
| 3 | 0.38 | 0.24 | | | | | | |
| 4 | 0.25 | 0.15 | | | | | | |
| 5 | 0.48 | 0.13 | | | | | | |
| 6 | 0.12 | 0.05 | <0.1 | <0.1 | 0 | 0 | 0.2 | 0.1 |
| 7 | 0.16 | 0.08 | <0.1 | <0.1 | 0 | 0 | 0.2 | 0.2 |
| 8 | 0.22 | 0.09 | <0.1 | <0.1 | 0 | 0.02 | 0.2 | 0.2 |
| 9 | 0.33 | 0.17 | <0.1 | <0.1 | 0 | 0 | 0.2 | 0.2 |

Experiment Set 6

An analyzer as depicted in FIG. 5 was employed for measurement of reflectance of whole blood in dependence of the hematocrit concentration. In this particular experiment, analyzer 400 had a housing 410 and actuator assembly 412. Holding pins 414 retained container 200 (see also FIG. 4) in a predetermined position relative to the actuator assembly 412, photomultiplier 442, and scatter unit 450. The scatter unit 450 included a first optical fiber port 452 that retained an optical fiber, wherein the fiber was anchored in the fiber port 452 such that one end of the fiber contacted the container (having one transparent side) and illuminated whole blood disposed within the container, while the other end of the optical fiber was illuminated by a laser diode with a wavelength maximum of 632 nm.

The scatter unit 450 further included a second optical fiber port 454 that retained another optical fiber, wherein the fiber was anchored in the fiber port 454 such that one end of the fiber contacted the container (having one transparent side) and received light scattered by the cells in the whole blood, while the other end of the optical fiber was optically coupled to a photodiode. The signal of the photodiode was electronically amplified and recorded using standard equipment well known in the art.

Figure 7A:
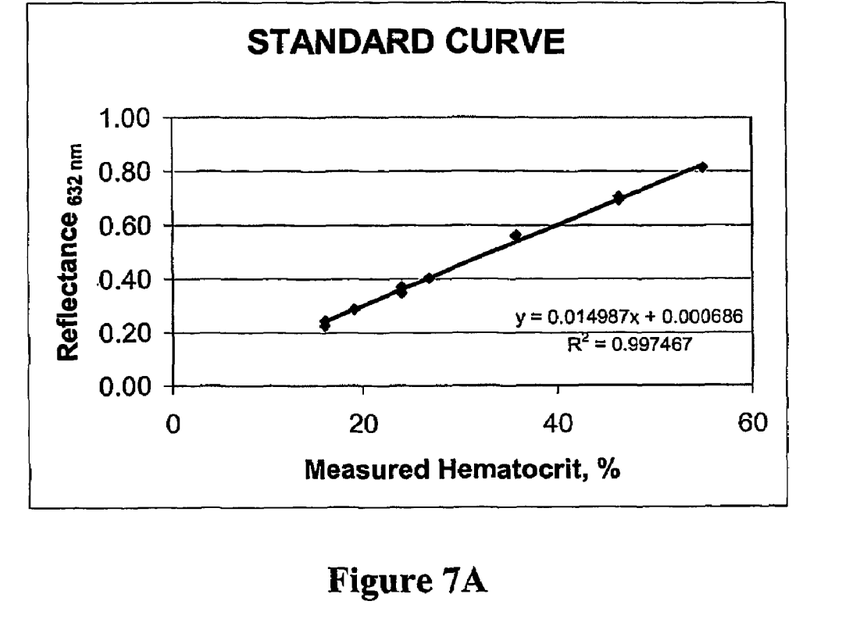
FIG. 7A is a graph depicting a standard curve of measured hematocrit against a reflectance signal obtained using an analyzer according to the inventive subject matter.

To determine a correlation between hematocrit concentration and reflectance in such configurations, whole blood samples with known hematocrit concentrations were individually placed into the container and illuminated while the container was disposed in the analyzer. The results of this experiment are depicted in FIG. 7A, in which reflectance was found to be a linear function of hematocrit with a high correlation coefficient.

Experiment Set 7

Figure 7B:
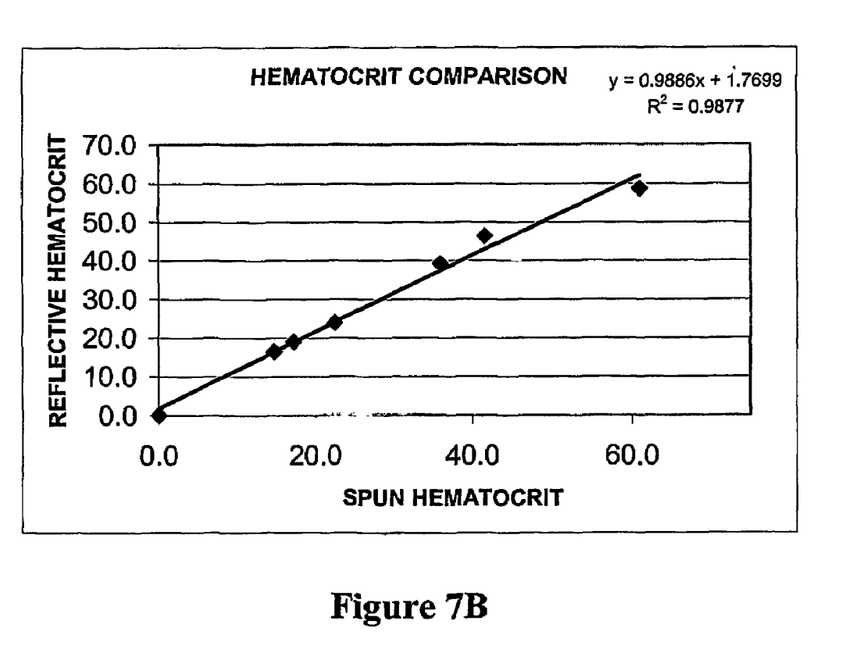
FIG. 7B is a graph depicting a correlation between spun hematocrit and hematocrit determined using a reflectance signal in an analyzer according to the inventive subject matter.

Using the analyzer of the previous experiment, whole blood samples with known hematocrit concentrations were divided in two portions. One portion was spun and the hematocrit concentration determined in conventional manner. The other portion was placed into the container and hematocrit was determined as described above using the linear function of FIG. 7A. FIG. 7B depicts the correlation between the hematocrit measurement as determined by reflectance and the hematocrit measurement as determined by centrifugation. Again, a relatively high correlation coefficient confirmed that hematocrit can be accurately determined using reflectance in the analyzer of Experiment 6.

Experiment Set 8

Figure 8A:
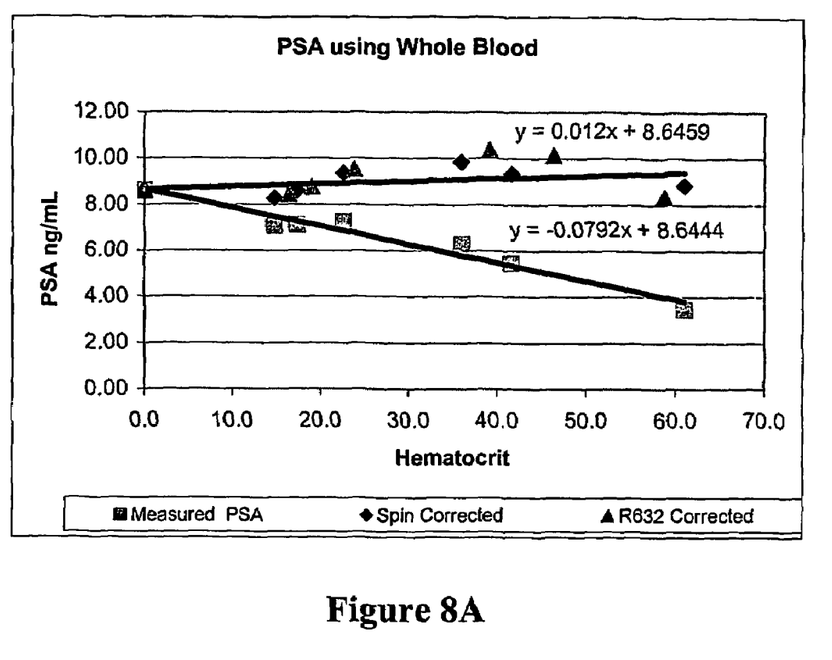
FIG. 8A is a graph depicting PSA measurements using various experimental parameters.

Using the analyzer of the previous experiment, free PSA (prostate specific antigen) was determined from whole blood using monoclonal antibodies whole blood samples with known hematocrit (here: between about 15-60%) and free PSA (here: between 8-10 ng/ml) concentrations. In a first set of experiments, the whole blood samples were employed for measurement without prior centrifugation to remove cellular components. As expected and can be seen from FIG. 8A, the actual PSA signal decreased with increasing hematocrit concentrations. In contrast, where the blood samples were centrifuged to remove cellular components, the PSA concentration remained at the expected levels. Similarly, where the blood samples were not centrifuged, but normalized using the correlation established from the experiments 6 and 7 above, the PSA concentration remained at substantially the same level, and showed high correlation to the centrifuged blood samples.

Of course, it should be recognized that the analytes that can be detected using methods and configurations according to the inventive subject matter need not be restricted to free PSA. It is generally contemplated that all analytes (and especially analytes that are dissolved or disposed in whole blood) for which a calorimetric, luminometric, or fluorimetric assay is available are considered suitable. For example, suitable analytes will include peptides (e.g., viral antigens, growth factors, CEA, etc.), hormones (e.g., TSH or testosterone), nucleic acids (e.g., tumor associated nucleic acids), small molecules (e.g., Schedule I-IV drugs, T4/T4 thyroxin, etc.).

Experiment Set 9

Figure 8B:
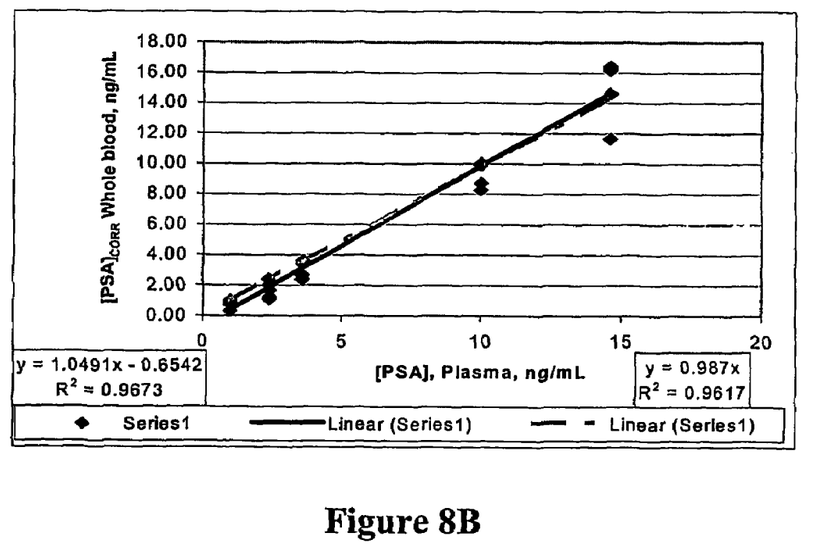
FIG. 8B is a graph depicting a correlation between PSA measurement from whole blood using a reflectance signal obtained using an analyzer according to the inventive subject matter and PSA measurement from previously prepared plasma.

Using the analyzer and correlations determined in the previous experiments, free PSA was determined over a range of PSA concentrations in samples over a range of hematocrit concentrations. Whole blood was used as starting material for two sets of experiments. In a first set of experiments, free PSA was determined from whole blood without removal of the cellular components using reflectance and correction factors obtained from the previously determined correlations. In a second set of experiments, free PSA was determined from whole blood after removal of cellular components. As can be clearly seen in FIG. 8B, there is an excellent correlation between the two experiments. Consequently, it should be appreciated that free PSA can be determined from whole blood in contemplated configurations without prior removal of cellular components, which will allow a physician to perform a free PSA test in his of her office without a requirement of an otherwise need permit to process (e.g., centrifuge) whole blood.

Consequently, the inventors contemplate a method of testing a cell-containing sample for a analyte in which in one step a container is provided wherein the container has a plurality of fluidly discontinuous compartments, including a sample reacting compartment, different first and second reagents contained in first and second reagent compartments, respectively, and a signal detection compartment. In another step, a cell-containing sample is placed into the sample reacting compartment, and the cell-containing sample is illuminated in the container thereby creating a light scatter signal (a light scatter signal is acquired). In a still further step, a surface of the container is contacted with a device having a plurality of actuators, and multiple different sets of the actuators are operated to independently add the first and second reagents to the sample in a variable sequence and time delay. In yet another step, at least a portion of the reacted sample is moved between the sample reacting compartment and the sample detection compartment using at least one of the sets of actuators, and an analyte-dependent signal is read from the reacted sample contained in the sample detection compartment, and a test result is calculated using the analyte-dependent signal and the light scatter signal.

Viewed from another perspective, the inventors therefore contemplate a method of manipulating a container in which a container is provided having a reaction channel fluidly coupled to a plurality of compartments, including a sample receiving compartment and a signal detection compartment, wherein at least one of the compartments includes a reagent. In another step, a cell-containing sample is introduced into the sample receiving compartment, and the cell-containing sample is illuminated in the container thereby creating a light scatter signal, which is acquired. In yet another step, a first portion of a surface of the container is contacted with a device having a plurality of independently operable actuators, wherein at least one of the actuators compresses a portion of the container thereby.moving at least part of the sample into the reaction channel, and in yet another step, a second portion of the surface of the container is contacted with another one of the actuators that compresses a portion of the container thereby preventing a movement of at least one of the part of the sample and the reagent between at least two of the plurality of compartments. In still another step, an analyte-dependent signal is read from the reacted sample contained in the sample detection compartment, and a test result is calculated using the analyte-dependent signal and the light scatter signal.

Thus, specific embodiments and applications of magnetic separation have been disclosed. It should be apparent to those skilled in the art, however, that many more modifications besides those already described are possible without departing from the inventive concepts herein. The inventive subject matter, therefore, is not to be restricted except in the spirit of the appended claims.

What is claimed is:

1. A method of testing a cell-containing sample for an analyte, comprising:
    providing a container having a plurality of fluidly discontinuous compartments, including a sample reacting compartment, different first and second reagents contained in first and second reagent compartments, respectively, and a signal detection compartment;
    receiving the cell-containing sample into the sample reacting compartment;
    illuminating the cell-containing sample in the container at a wavelength thereby creating a light scatter signal, reading the light scatter signal, and automatically calculating a hematocrit value using the light scatter signal and a predetermined linear relationship between reflectance and the hematocrit value at the wavelength;
    contacting a surface of the container with a device having a plurality of actuators;
    operating multiple different sets of the actuators to independently add the first and second reagents to the cell-containing sample in a variable sequence and time delay;
    moving at least a portion of the reacted cell-containing sample between the sample reacting compartment and the sample detection compartment using at least one of the sets of actuators; and
    reading an analyte-specific signal from the reacted cell-containing sample contained in the sample detection compartment, wherein the analyte-specific signal is a colorimetric, luminometric, or fluorimetric signal, and calculating a test result using the analyte-specific signal and the light scatter signal.

2. The method of claim 1 wherein the step of illuminating is performed using a light guide disposed in one of the actuators.

3. The method of claim 2 wherein the step of reading the light scatter signal is performed using another light guide disposed in the one of the actuators.

4. The method of claim 1 wherein the step of illuminating is performed using light having a wavelength maximum at between 620 nm and 660 nm.

5. The method of claim 1 wherein the container has a flexible top sheet and a flexible bottom sheet, wherein at least one of the compartments is formed by the flexible top sheet and bottom sheet, and wherein at least a portion of the top sheet and bottom sheet is transparent.

* * * * *